US009676817B2

(12) United States Patent
Johansen et al.

(10) Patent No.: US 9,676,817 B2
(45) Date of Patent: Jun. 13, 2017

(54) METHOD FOR THE REMOVAL OF VIRUS FROM A PROTEIN SOLUTION

(71) Applicant: Novozymes A/S, Bagsvaerd (DK)

(72) Inventors: Poul Johansen, Virum (DK); Cecilia Jansson Kepka, Bunkeflostrand (SE)

(73) Assignee: Novozymes A/S

( * ) Notice: Subject to any disclaimer, the term of this patent is extended or adjusted under 35 U.S.C. 154(b) by 0 days.

(21) Appl. No.: 14/364,928

(22) PCT Filed: Dec. 19, 2012

(86) PCT No.: PCT/EP2012/076194
§ 371 (c)(1),
(2) Date: Jun. 12, 2014

(87) PCT Pub. No.: WO2013/092741
PCT Pub. Date: Jun. 27, 2013

(65) Prior Publication Data
US 2014/0335594 A1 Nov. 13, 2014

(30) Foreign Application Priority Data

Dec. 20, 2011 (EP) ..................................... 11194674

(51) Int. Cl.
| | |
|---|---|
| C07K 1/36 | (2006.01) |
| C07K 1/30 | (2006.01) |
| A61L 2/00 | (2006.01) |
| C07K 1/00 | (2006.01) |

(52) U.S. Cl.
CPC .............. *C07K 1/30* (2013.01); *A61L 2/0011* (2013.01)

(58) Field of Classification Search
CPC ........ A61K 38/00; A61K 48/00; A61K 31/70; A61K 2300/00; A61K 36/48; A61K 31/704; A61K 41/0038; A61K 31/198; A61K 31/405; A61K 31/43; A61K 31/57; A61K 31/573; A61K 31/65; A61K 38/10; A61K 47/48207; A61K 9/1682; A61K 35/76; A61K 38/08; A61K 38/14; C08L 83/12; C12N 15/86; C12N 2795/00032; C12N 2795/00043; C12N 2830/60; C12N 2750/12022; C12N 2810/40; C12N 2810/60; C12N 2830/008; C12N 2840/203; C12N 2740/16062; C12N 2799/025; C12N 2799/027; C12N 2830/00; Y10T 428/31612; Y10T 428/31663; Y10T 436/143333; Y10T 436/105831; C12P 21/02; C07K 2319/036; A23K 20/189; A01N 25/10; D06M 16/003; Y02W 30/648; A61Q 11/00

See application file for complete search history.

(56) References Cited

U.S. PATENT DOCUMENTS

| | | | |
|---|---|---|---|
| 3,817,834 A | 6/1974 | Wilson | |
| 6,468,778 B1 | 10/2002 | Schueler | |
| 7,393,928 B2 * | 7/2008 | Chang | A23L 1/05625 435/320.1 |
| 2011/0237781 A1 | 9/2011 | Lebing | |

FOREIGN PATENT DOCUMENTS

| | | |
|---|---|---|
| CN | 101575365 | 11/2009 |
| EP | 1 250 929 | 10/2002 |
| WO | 02/04615 A1 | 1/2002 |
| WO | 03100080 A2 | 12/2003 |

OTHER PUBLICATIONS

Fic. et al. Electrophoresis 2010, vol. 31, pp. 3573-3579.*
Ward et al. Current Analytical Chemistry, 2009, vol. 5, pp. 1-21.*
Cazin, JR. Journal of Bacteriology, 1069, vol. 100, No. 2, pp. 760-762.*
Trypsin in Worthington Enzyme Manual published by VWorthington Biochemical Corporation. (730 Vassar Ave., Lakewood, NJ 08701, 2016, pp. 1-3.*
Chymotrypsin in Worthington Enzyme Manual published by VWorthington Biochemical Corporation. (730 Vassar Ave., Lakewood, NJ 08701, 2016, pp. 1-3.*
Deoxyribonuclease I in Worthington Enzyme Manual, published byVWorthington Biochemical Corporation. (730 Vassar Ave., Lakewood, NJ 08701, 2016, pp. 1-3.*
Yang et al. RNA published in 2007, vol. 13, pp. 682-690.*
Welles et al, Transfusion, vol. 26, No. 2, pp. 210-213 (1986).
WHO Technical Report Series, No. 924 (Jan. 1, 2004), pp. 151-224.
Kitamura et al, 2000, Bulletin of Tokyo Kasei University, vol. 40, No. 2, pp. 53-56.
Chen et al, 2008, China Light Industry Press, pp. 302.

* cited by examiner

*Primary Examiner* — Bao Li
(74) *Attorney, Agent, or Firm* — Kristin McNamara

(57) ABSTRACT

The author attempted and succeeded in separating and purifying the cysteine protease inhibitors from new gingers. The root and stem of new gingers were extracted with neutral buffer which subsequently underwent heat treatment at 80° C. for 10 minutes. After centrifugal separation, the supernatant was separated with acetone. The fractions that precipitated at an acetone concentration of 55-77% were injected into a chromatographic column of DEAE-cellulose and Sephadex G-75 gel for purification. The results demonstrated that there were two cysteine protease inhibitors with a molecular weight of 11,000-11,800 and 15,500-16,000, respectively, which strongly inhibit papain. The two cysteine protease inhibitors do not have high heat stability.

19 Claims, No Drawings

METHOD FOR THE REMOVAL OF VIRUS FROM A PROTEIN SOLUTION

CROSS-REFERENCE TO RELATED APPLICATIONS

This application is a 35 U.S.C. 371 national application of PCT/EP2012/076194 filed Dec. 19, 2012 which claims priority or the benefit under 35 U.S.C. 119 of European application no. 11194674.5 filed Dec. 20, 2011 and U.S. provisional application no. 61/579,281 filed Dec. 22, 2011 the contents of which are fully incorporated herein by reference.

FIELD OF THE INVENTION

The present invention relates to a method for purification of a protein.

BACKGROUND OF THE INVENTION

Proteins isolated from animal sources are susceptible to being contaminated with virus particles and/or virus DNA which is unwanted when the proteins are to be used, e.g., in food or pharmaceutical products. Methods are known for purification of such proteins which will also reduce the level of virus particles and/or virus DNA, such as chromatography, filtration, centrifugation, extraction or precipitation. However, in some cases, the purification of a protein of interest is difficult, time-consuming and/or expensive. It is therefore an object of the present invention to provide a method for removing from a protein of interest any contaminating virus particles and/or virus DNA. Such method should be fast, useful in industrial scale, inexpensive and effective.

Trypsin (EC 3.4.21.4) is a serine protease found in the digestive system of many vertebrates where it hydrolyses proteins. Trypsin is available in high quantity in the pancreas of mammals and, e.g., porcine and bovine trypsin can be purified rather easily. Hence, trypsin has been used widely in various biotechnological processes. Further, trypsin is used in baby food to pre-digest the protein.

Porcine circovirus type 2 (PCV2) is a small non-enveloped virus which replicates autonomously in eukaryotic cells. It is the etiological agent of Postweaning Multisystemic Wasting Syndrome (PMWS), a new emerging and multifactorial disease in swine.

It is an object of the present invention to provide a method for removing PCV2 virus particles and/or virus DNA from trypsin extracted from porcine pancreatic glands.

SUMMARY OF THE INVENTION

The invention provides a method for selectively removing virus and/or virus DNA from an aqueous solution comprising a target protein, said method comprising:
a) adding acetone to the solution at a concentration which selectively precipitates the virus and/or virus DNA,
b) performing a separation step to separate precipitated material from the solution comprising the target protein,
c) adding to the solution an additional amount of acetone to reach a final concentration which precipitates the target protein, and
d) collecting the precipitated target protein from the solution.

DETAILED DESCRIPTION OF THE INVENTION

The present invention provides a method for selectively removing virus and/or virus DNA from an aqueous solution comprising a target protein, said method comprising:
a) adding acetone to the solution at a concentration which selectively precipitates the virus and/or virus DNA,
b) performing a separation step to separate precipitated material from the solution comprising the target protein,
c) adding to the solution an additional amount of acetone to reach a final concentration which precipitates the target protein, and
d) collecting the precipitated target protein from the solution.

For the avoidance of any possible doubt: The steps are performed in the order written. I.e., the separation in step b) is performed to separate the precipitated material of step a) from the solution comprising the target protein. In step c), an additional amount of acetone is added to the solution obtained in step b). And in step d), the precipitated target protein of step c) is collected from the solution.

The target protein may be any protein. It may be a protein which has been isolated from a microorganism, e.g., from bacterial or fungal cells. It may be a protein which has been isolated from a plant. Preferably, it is a protein which has been isolated from an animal source. Such protein may be susceptible to having been contaminated with virus particles and/or virus DNA which, e.g., originate from the source organism from which the protein was expressed.

The target protein may have been obtained from a mammalian source. It may have been obtained from mammalian tissue, e.g., from a mammalian gland. In a preferred embodiment, the target protein has been obtained from bovine or porcine pancreas. In a more preferred embodiment, the target protein has been obtained from porcine pancreas.

The target protein may be an enzyme, preferably an active enzyme or an enzyme which can be reactivated.

Enzymes which may be obtained from mammalian pancreas, e.g., from porcine pancreas, include, but are not limited to, proteases including, but not limited to, trypsin, chymotrypsin, chymotrypsin B, pancreatopeptidase E, carboxypeptidase A and carboxypeptidase B; lipases, including, but not limited to, glycerol ester hydrolase (lipase), phospholipase A1, phospholipase A2 and sterol ester hydrolase; nucleases, including, but not limited to, ribonuclease and deoxyribonuclease; amylases, including, but not limited to, alpha-amylase.

In a preferred embodiment, the target protein is a protease, preferably a protease obtained from a mammalian source, e.g., from pancreas, preferably from bovine or porcine pancreas, more preferably from porcine pancreas.

In a more preferred embodiment, the target protein is trypsin, preferably trypsin obtained from pancreas, more preferably trypsin obtained from bovine or porcine pancreas, even more preferably trypsin obtained from porcine pancreas.

The aqueous solution comprising the target protein preferably has a low conductivity, e.g., below 3 mS or below 1 mS. This may be obtained, e.g., by diafiltration, e.g., using a membrane with a cut off of 10,000 Da. The aqueous solution comprising the target protein preferably has a pH of about 2-5, e.g., about 3-4, preferably about 3.1-3.9, such as about 3.5.

The dry matter concentration of the aqueous solution may be about 8-20%, e.g. about 8-15%, such as about 10%.

In the method of the invention, virus and/or virus DNA is selectively removed from an aqueous solution comprising a target protein. The virus may be virus particles. I.e., in a preferred embodiment, the method is for selectively removing virus particles and/or virus DNA from an aqueous solution comprising a target protein. In a more preferred embodiment, the method is for selectively removing virus DNA from an aqueous solution comprising a target protein.

The virus may be an infectious virus, e.g., an infectious virus found in porcine sources.

The virus may be a DNA virus, e.g. a single-stranded DNA virus, such as a virus with single-stranded and circular DNA. The virus may be an RNA virus.

The virus may be a non-enveloped virus, e.g., a small non-enveloped virus. It may be a non-enveloped DNA virus or a non-enveloped RNA virus.

The virus may be a virus which replicates autonomously in eukaryotic cells.

In a preferred embodiment, the virus is a non-enveloped DNA virus, e.g., a small non-enveloped DNA virus.

The virus may be selected from the group consisting of PCV2 (porcine circovirus 2), PCV1 (porcine circovirus 1), PPV (porcine parvovirus), EMCV (porcine encephalomyocarditis virus), HEV (swine hepatitis E virus) and SVDV (swine vesicular disease virus). In a preferred embodiment, the virus is PCV2.

In step a) of the method of the invention, acetone is added to the solution comprising the target protein at a concentration which selectively precipitates the virus and/or virus DNA. It may be virus particles comprising or associated with virus DNA which precipitate. And/or it may be virus DNA as such, e.g., free virus DNA, which precipitates.

By selective precipitation is meant that the majority of the virus and/or the virus DNA is precipitated, i.e. more than 50%, while less than 50% of the target protein is precipitated.

Preferably, at least 60%, such as at least 70%, at least 80% or at least 90%, of the virus DNA is precipitated in step a). More preferably, at least 95%, such as at least 99% or at least 99.9%, of the virus DNA is precipitated in step a).

Preferably, less than 40%, such as less than 30%, of the target protein is precipitated in step a). More preferably, less than 25%, such as less than 20%, less than 10% or less than 5%, of the target protein is precipitated in step a).

The skilled person will know how to determine the concentration of acetone to be used in step a). In a preferred embodiment, the concentration of acetone in step a) is about 12-40% (v/v), preferably about 12-30% (v/v), more preferably about 14-30% (v/v), even more preferably about 15-20% (v/v). In a more preferred embodiment, the target protein is trypsin and the concentration of acetone in step a) is about 12-40% (v/v), preferably about 12-30% (v/v), more preferably about 14-30% (v/v), even more preferably about 15-20% (v/v). In an even more preferred embodiment, the target protein is trypsin, the virus is PCV2 and the concentration of acetone in step a) is about 12-40% (v/v), preferably about 12-30% (v/v), more preferably about 14-30% (v/v), even more preferably about 15-20% (v/v).

Preferably, the selective precipitation in step a) is performed at a temperature below 15° C. Step b) in the method of the invention is a separation step wherein the material which has been precipitated in step a) is separated from the solution comprising the target protein. Such separation may be performed by any method known in the art. The separation may comprise filtration and/or centrifugation. In a preferred embodiment, the separation in step b) comprises depth filtration.

Preferably, at least 50%, such as at least 60%, at least 70%, at least 80% or at least 90%, of the virus DNA is separated in step b). More preferably, at least 95%, such as at least 99% or at least 99.9%, of the virus DNA is separated in step b).

In one preferred embodiment, no virus DNA can be detected in the solution comprising the target protein after the precipitated material has been separated in step b).

Preferably, less than 40%, such as less than 30%, of the target protein is separated in step b). More preferably, less than 25%, such as less than 20%, less than 10% or less than 5%, of the target protein is separated in step b).

Preferably, more than 60%, such as more than 70%, of the target protein is recovered in the solution after the separation in step b). More preferably, more than 75%, such as more than 80%, more than 90% or more than 95%, of the target protein is recovered in the solution after the separation in step b).

Preferably, more than 60%, such as more than 70%, of the target protein is recovered in its active form in the solution after the separation in step b). More preferably, more than 75%, such as more than 80%, more than 90% or more than 95%, of the target protein is recovered in its active form in the solution after the separation in step b).

After step b), pH of the filtrate may be adjusted to, e.g., about pH 4-5, such as about pH 4.5. Any base, preferably a weak base, e.g., ammonia water, may be used.

In step c) in the method of the invention, an additional amount of acetone is added to the solution comprising the target protein. The acetone is added to reach a final concentration which precipitates the target protein.

Preferably, more than 60%, such as more than 70% or more than 80%, of the target protein present in the solution after step b) is precipitated in step c). More preferably, more than 90%, such as more than 95%, more than 98% or more than 99%, of the target protein present in the solution after step b) is precipitated in step c).

The skilled person will know how to determine the concentration of acetone to be used in step c). In a preferred embodiment, the final concentration of acetone in step c) is 45-95%, preferably 60-70% (v/v), more preferably about 66% (v/v). In another preferred embodiment, the concentration of acetone in step a) is about 12-40% (v/v), preferably about 12-30% (v/v), more preferably about 14-30% (v/v), even more preferably about 15-20% (v/v), and the final concentration of acetone in step c) is 45-95%, preferably 60-70% (v/v), more preferably about 66% (v/v). In a more preferred embodiment, the target protein is trypsin, the concentration of acetone in step a) is about 12-40% (v/v), preferably about 12-30% (v/v), more preferably about 14-30% (v/v), even more preferably about 15-20% (v/v), and the final concentration of acetone in step c) is 45-95%, preferably 60-70% (v/v), more preferably about 66% (v/v). In an even more preferred embodiment, the target protein is trypsin, the virus is PCV2, the concentration of acetone in step a) is about 12-40% (v/v), preferably about 12-30% (v/v), more preferably about 14-30% (v/v), even more preferably about 15-20% (v/v), and the final concentration of acetone in step c) is 45-95%, preferably 60-70% (v/v), more preferably about 66% (v/v).

Preferably, step c) is performed at a temperature below 15° C.

In step d) in the method of the invention, the precipitated target protein is collected from the solution. Such collection of the precipitated target protein may be performed by any method known in the art. The collection of the precipitated target protein may comprise filtration and/or centrifugation.

After having been collected, the target protein may be washed, dried, grinded and/or standardized.

In a preferred embodiment, the present invention relates to a method for selectively removing PCV2 virus and/or PCV2 virus DNA from a preparation of porcine trypsin, preferably porcine pancreatic trypsin, said method comprising:
  a) adding acetone to an aqueous solution comprising the trypsin to reach an acetone concentration of 12-30% (v/v),
  b) performing a separation step to separate precipitated material from the solution comprising trypsin,
  c) adding to the solution an additional amount of acetone to reach a final concentration of 45-95% (v/v), preferably 60-70% (v/v), and
  d) collecting the precipitated trypsin from the solution.

Preferably, at least 50%, such as at least 60%, at least 70%, at least 80% or at least 90%, of the virus DNA is separated from the target protein by the method of the invention. More preferably, at least 95%, such as at least 99% or at least 99.9%, of the virus DNA is separated from the target protein by the method of the invention.

Preferably, target protein which has been purified by the method of the invention comprises less than 50% virus DNA as compared to target protein which has been purified in the same way but without steps a) and b) of the method. More preferably, target protein which has been purified by the method of the invention comprises less than 40%, such as less than 30%, less than 20% or less than 10%, virus DNA as compared to target protein which has been purified in the same way but without steps a) and b) of the method. Even more preferably, target protein which has been purified by the method of the invention comprises less than 5%, such as less than 1%, less than 0.5% or less than 0.1%, virus DNA as compared to target protein which has been purified in the same way but without steps a) and b) of the method.

In one preferred embodiment, the precipitated target protein collected in step d) comprises no detectable virus DNA.

Detection or quantification of virus DNA may be performed by any method known in the art. Real-time PCR may be used.

DNA may be extracted using lysis incubation followed by a DNA extraction in equal volume chloroform. DNA may be finally purified and concentrated using commercially available DNA kits. Presence of virus DNA may be subsequently detected using Real-time PCR.

In a preferred embodiment, the virus is PCV2 and Real-time PCR is performed using a commercially available PCV2 detection kit.

The general principle of DNA quantification by Real-time PCR relies on plotting fluorescence against the number of cycles on a logarithmic scale. A threshold for detection of DNA-based fluorescence is set slightly above background and the cycle threshold (Ct) is defined as the number of cycles required for the fluorescent signal to cross the threshold (i.e. exceed background level). During the exponential amplification phase, the sequence of the DNA target doubles every cycle. For example, a DNA sample whose Ct precedes that of another sample by 3 cycles contained $2^3=8$ times more template.

In one embodiment, the amount of virus DNA which can be detected in total DNA extracted from precipitated target protein collected in step d), when analyzed in a Real-time PCR assay undergoing 40 cycles of amplification and using a primer which is specific for the relevant virus DNA, results in a Ct value of at least 38, preferably at least 39, more preferably 40.

A Ct value of 40 means that after 40 cycles of amplification, the threshold for detection of DNA-based fluorescence is not exceeded, i.e. a signal is never detected. Also, Ct values slightly below 40 are very likely to be false positive and therefore do not equal detection of virus DNA.

In a preferred embodiment, the virus is PCV2 and the amount of PCV2 DNA which can be detected in total DNA extracted from precipitated target protein collected in step d), when analyzed in a Real-time PCR assay undergoing 40 cycles of amplification and using a primer which is specific for PCV2 DNA, results in a Ct value of at least 38, preferably at least 39, more preferably 40.

EXAMPLES

Example 1

Source: A PCV2 positive trypsin batch derived by aqueous extraction of porcine pancreatic glands.

The trypsin batch was dissolved in cold tap water to an 11% solution. pH in the solution was adjusted to 3.5 by addition of hydrochloric acid. Acetone was added to a final concentration of 20% v/v, followed by addition of 1% filter aid (Kieselguhr Hyflo Super Cel®). Under the addition of acetone and filter aid the solution was stirred and the temperature kept under 15° C. Subsequently the unclear solution was filtered on a filter press with acetone resistant filter clothes (polypropylene) and germ filter sheets. (Seitz EKS). The pressure was kept under 1.8 bar during the filtration. The impurities which were retained on the filter were discharged. The clear filtrate was collected in a tank and pH was adjusted to 4.5 with ammonia water. Acetone was added to a final concentration of 66% v/v. Under the addition of acetone the solution was stirred and the temperature kept under 15° C. A precipitate appeared (trypsin). The precipitate was collected by filtration on a filter press with acetone resistant filter clothes (polypropylene). The pressure was kept under 3.5 bar during the filtration. Finally the precipitate was dried in a vacuum drier. The end pressure was 0.5 millibar and the end temperature 38° C.

DNA was extracted using lysis incubation followed by a DNA extraction in equal volume chloroform. DNA was finally purified and concentrated using commercially available DNA kits. Presence of PCV2 DNA was subsequently analyzed in a RealTime PCR instrument using a commercially available PCV2 detection kit. The dried trypsin was found negative for PCV2.

Example 2

Source: A PCV2 positive liquid trypsin batch derived by aqueous extraction of porcine pancreatic glands. Filter aid (Kieselguhr Hyflo Super Cel®) has been added and filtration performed on a filter press with Seitz HS9000 filter pads. The filtrate has been diafiltered (using a membrane with a cut off of 10,000 Da) until the conductivity was below 1 mS. The concentration has been adjusted to 10% dry matter and pH adjusted to 3.5 with hydrochloric acid. The batch was divided into 2 equal parts.

a) Acetone was added to a final concentration of 15% v/v, followed by addition of 1% filter aid (Kieselguhr Hyflo Super Cel®). Under the addition of acetone and filter aid the solution was stirred and the temperature kept under 15° C. Subsequently the unclear solution was filtered on a filter press with acetone resistant filter clothes (polypropylene) and germ filter sheets (Seitz EKS). The pressure was kept under 1.8 bar during the filtration. The impurities which were retained on the filter were discharged. The clear filtrate was collected in a tank and pH was adjusted to 4.5 with ammonia water. Acetone was added to a final concentration of 66% v/v. Under the addition of acetone the solution was stirred and the temperature kept under 15° C. A precipitate appeared (trypsin). The precipitate was collected by filtration on a filter press with acetone resistant filter clothes (polypropylene). The pressure was kept under 3.5 bar during the filtration. Finally the precipitate was dried in a vacuum drier. The end pressure was 0.5 millibar and the end temperature 38° C.

DNA was extracted using lysis incubation followed by a DNA extraction in equal volume chloroform. DNA was finally purified and concentrated using commercially available DNA kits. Presence of PCV2 DNA was subsequently analyzed in a RealTime PCR instrument using a commercially available PCV2 detection kit. The dried trypsin was found negative for PCV2 (Ct: 40).

b) 1% filter aid (Kieselguhr Hyflo Super Cel®) was added to the solution. Under the addition of filter aid the solution was stirred and the temperature kept under 15° C. Subsequently the unclear solution was filtered on a filter press with acetone resistant filter clothes (polypropylene) and germ filter sheets (Seitz EKS). The pressure was kept under 1.8 bar during the filtration. The impurities which were retained on the filter were discharged. The clear filtrate was collected in a tank and pH in was adjusted to 4.5 with ammonia water. Acetone was added to a final concentration of 66% v/v. Under the addition of acetone the solution was stirred and the temperature kept under 15° C. A precipitate appeared (trypsin). The precipitate was collected by filtration on a filter press with acetone resistant filter clothes (polypropylene). The pressure was kept under 3.5 bar, during the filtration. Finally the precipitate was dried in a vacuum drier. The end pressure was 0.5 millibar and the end temperature 38° C.

DNA was extracted using lysis incubation followed by a DNA extraction in equal volume chloroform. DNA was finally purified and concentrated using commercially available DNA kits. Presence of PCV2 DNA was subsequently analyzed in a RealTime PCR instrument using a commercially available PCV2 detection kit. The dried trypsin was found positive for PCV2 (Ct: 36).

Example 3

Source: A PCV2 positive liquid trypsin batch derived by aqueous extraction of porcine pancreatic glands. Filter aid (Kieselguhr Hyflo Super Cel®) has been added and filtration performed on a filter press with Seitz HS9000 filter pads. The filtrate has been diafiltered (using a membrane with a cut off of 10,000 Da) until the conductivity was below 1 mS. The concentration has been adjusted to 10% dry matter and pH adjusted to 3.5 with hydrochloric acid. The batch was divided into 2 equal parts.

a) Acetone was added to a final concentration of 10% v/v, followed by addition of 1% filter aid (Kieselguhr Hyflo Super Cel®). Under the addition of acetone and filter aid the solution was stirred and the temperature kept under 15° C. Subsequently the unclear solution was filtered on a filter press with acetone resistant filter clothes (polypropylene) and germ filter sheets (Seitz EKS). The pressure was kept under 1.8 bar during the filtration. The impurities which were retained on the filter were discharged. The clear filtrate was collected in a tank and pH was adjusted to 4.5 with ammonia water. Acetone was added to a final concentration of 66% v/v. Under the addition of acetone the solution was stirred and the temperature kept under 15° C. A precipitate appeared (trypsin). The precipitate was collected by filtration on a filter press with acetone resistant filter clothes (polypropylene). The pressure was kept under 3.5 bar during the filtration. Finally the precipitate was dried in a vacuum drier. The end pressure was 0.5 millibar and the end temperature 38° C.

DNA was extracted using lysis incubation followed by a DNA extraction in equal volume chloroform. DNA was finally purified and concentrated using commercially available DNA kits. Presence of PCV2 DNA was subsequently analyzed in a RealTime PCR instrument using a commercially available PCV2 detection kit. The dried trypsin was found positive for PCV2 (Ct: 35).

b) 1% filter aid (Kieselguhr Hyflo Super Cel®) was added to the solution. Under the addition of filter aid the solution was stirred and the temperature kept under 15° C. Subsequently the unclear solution was filtered on a filter press with acetone resistant filter clothes (polypropylene) and germ filter sheets (Seitz EKS). The pressure was kept under 1.8 bar during the filtration. The impurities which were retained on the filter were discharged. The clear filtrate was collected in a tank and pH was adjusted to 4.5 with ammonia water. Acetone was added to a final concentration of 66% v/v. Under the addition of acetone the solution was stirred and the temperature kept under 15° C. A precipitate appeared (trypsin). The precipitate was collected by filtration on a filter press with acetone resistant filter clothes (polypropylene). The pressure was kept under 3.5 bar during the filtration. Finally the precipitate was dried in a vacuum drier. The end pressure was 0.5 millibar and the end temperature 38° C.

DNA was extracted using lysis incubation followed by a DNA extraction in equal volume chloroform. DNA was finally purified and concentrated using commercially available DNA kits. Presence of PCV2 DNA was subsequently analyzed in a RealTime PCR instrument using a commercially available PCV2 detection kit. The dried trypsin was found positive for PCV2 (Ct: 36).

The invention claimed is:

1. A method for selectively removing virus and/or virus DNA from an aqueous solution comprising a target protein selected from the group consisting of trypsin, chymotrypsin, chymotrypsin B, or a mixture thereof, said method comprising:
   a) adding acetone to the solution at a concentration which selectively precipitates the virus and/or virus DNA, wherein the concentration of acetone is 12-40% (v/v),
   b) performing a separation step to separate precipitated material from the solution comprising the target protein,
   c) adding to the solution an additional amount of acetone to reach a final concentration which precipitates the target protein, wherein the final concentration of acetone is 45-95% (v/v), and
   d) collecting the precipitated target protein from the solution.

2. The method of claim 1, wherein the concentration of acetone in step a) is about 12-30% (v/v).

3. The method of claim 1, wherein the concentration of acetone in step a) is about 14-30% (v/v).

4. The method of claim 1, wherein the concentration of acetone in step a) is about 15-20% (v/v).

5. The method of claim 1, wherein the concentration of acetone in step a) is about 15% (v/v).

6. The method of claim 1, wherein the final concentration of acetone in step c) is 60-70% (v/v).

7. The method of claim 1, wherein the final concentration of acetone is about 66% (v/v).

8. The method of claim 1, wherein the target protein is trypsin.

9. The method of claim 1, wherein the selective precipitation in step a) is performed at a temperature below 15° C.

10. The method of claim 1, wherein the separation in step b) comprises filtration and/or centrifugation.

11. The method of claim 1, wherein the separation in step b) comprises depth filtration.

12. The method of claim 1, wherein step d) comprises filtration and/or centrifugation.

13. The method of claim 1, wherein the virus is a non-enveloped virus.

14. The method of claim 13, wherein the virus is PCV2.

15. A method for selectively removing virus and/or virus DNA from a preparation of trypsin, said method comprising:
   a) adding acetone to an aqueous solution comprising the trypsin to reach an acetone concentration of 12-30% (v/v),
   b) performing a separation step to separate precipitated material from the solution comprising trypsin,
   c) adding to the solution an additional amount of acetone to reach a final concentration of 45-95% (v/v) and
   d) collecting the precipitated trypsin from the solution.

16. The method of claim 15, comprising porcine trypsin.

17. The method of claim 15, comprising porcine pancreatic trypsin.

18. The method of claim 15, wherein the final concentration of acetone in step c) is 60-70% (v/v).

19. The method of claim 15, wherein the final concentration of acetone is about 66% (v/v).

* * * * *

UNITED STATES PATENT AND TRADEMARK OFFICE
CERTIFICATE OF CORRECTION

PATENT NO. : 9,676,817 B2
APPLICATION NO. : 14/364928
DATED : June 13, 2017
INVENTOR(S) : Johansen et al.

Page 1 of 1

It is certified that error appears in the above-identified patent and that said Letters Patent is hereby corrected as shown below:

On the Title Page

Above the Foreign Application Priority Data, please insert:
--Related U.S. Application Data
(60) Provisional application no. 61/579,281, filed on December 22, 2011--

Signed and Sealed this
Twenty-seventh Day of August, 2019

Andrei Iancu
*Director of the United States Patent and Trademark Office*